(12) United States Patent
O'Lenick, Jr. et al.

(10) Patent No.: US 7,834,116 B2
(45) Date of Patent: Nov. 16, 2010

(54) FLUORO SILICONE ACRYLATES AND POLYMERS THEREOF

(76) Inventors: Anthony John O'Lenick, Jr., 2170 Luke Edwards Rd., Dacula, GA (US) 30019; John Imperante, 109 Old Driftway La., Califon, NJ (US) 07830

( * ) Notice: Subject to any disclaimer, the term of this patent is extended or adjusted under 35 U.S.C. 154(b) by 130 days.

(21) Appl. No.: 12/378,051

(22) Filed: Feb. 11, 2009

(65) Prior Publication Data

US 2010/0204426 A1  Aug. 12, 2010

(51) Int. Cl.
*C08F 130/08* (2006.01)
*C08F 230/08* (2006.01)
*C08F 30/08* (2006.01)

(52) U.S. Cl. .................... 526/279; 556/439

(58) Field of Classification Search ............... None
See application file for complete search history.

(56) References Cited

U.S. PATENT DOCUMENTS

| 6,524,705 | B1 | 2/2003 | O'Lenick | |
| 6,846,568 | B2 * | 1/2005 | Yamaya et al. | 428/447 |
| 2006/0210727 | A1 * | 9/2006 | Ibuki et al. | 428/1.31 |

* cited by examiner

*Primary Examiner*—Daniel M Sullivan
*Assistant Examiner*—Chukwuma O Nwaonicha

(57) ABSTRACT

The present invention is directed to fluoro silicone acrylates that are used in reaction either alone or with other monomers to make polymers that can modify the surface of hair skin or pigment. This makes them ideal for incorporation into pigmented products in personal care applications like make up and lipsticks.

4 Claims, No Drawings

FLUORO SILICONE ACRYLATES AND POLYMERS THEREOF

FIELD OF THE INVENTION

The present invention is directed to fluoro silicone acrylates that are used in reaction either alone or with other monomers to make polymers that can modify the surface of hair skin or pigment. This makes them ideal for incorporation into pigmented products in personal care applications like make up and lipsticks.

BACKGROUND OF THE INVENTION

U.S. Publication 2008/0139765 published Jun. 12, 2008, incorporated herein by reference, describes particular copolymers with glass transition temperatures greater than 70° Celsius that demonstrate enhanced wear in combination with a smooth, non-tacky feel. This patent describes the method of polymerization of acrylates used in making the polymers of the present invention.

U.S. Pat. No. 6,245,924 issued Jun. 12, 2001 to Imperante discloses, incorporated herein by reference, discloses a series of novel quaternized silicone fluorinated dimethicone copolyol phosphates. These materials do not contain the reactive acrylate group and do contain a water-soluble group.

U.S. Pat. No. 6,747,116 issued Jun. 8, 2004 to O'Lenick et al, incorporated herein by reference, discloses a novel dimethicone copolyol phosphate ester compounds bearing a fluoro group attached through a hydrophobic ester linkage to silicon. This invention also relates a series of such products having differing amounts of water-soluble groups, silicone soluble groups and fatty soluble groups.

U.S. Pat. No. 6,524,705 to O'Lenick et al, incorporated herein by reference, teaches the treatment of metal oxide particles with a novel silanic hydrogen containing silicone, that provide metal oxide particles that have modified dispersibility in a variety of solvents, including silicone fluid, mineral oil, and fluoro solvents.

The above references show that there is a long felt, unsatisfied need for using fluoro compounds together with silicone compounds to provide modified surfaces that have desirable properties. None of the compounds of the art cited posses the required acrylate group, allowing for a subsequent step of free radical polymerization in solvent to make highly prized silicone film formers. Some examples cited above also possess the undesirable groups like water-soluble groups.

DETAILED DESCRIPTION OF THE INVENTION

One aspect of the preset invention is drawn to a novel fluoro silicone acrylate conforming to the following structure:

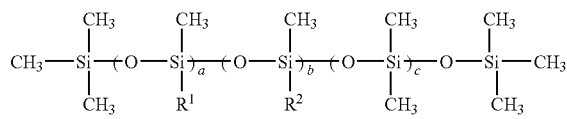

wherein
$R^1$ is —$(CH_2)_2$—$(CF_2)_8$—$CF_3$
$R^2$ is
    —$(CH_2)_3$—O—C(O)—CH=$CH_2$
a is an integer ranging from 1 to 20;
b is an integer ranging from 1 to 4;
c is an integer ranging from 0 to 20.

Class 1 Monomer
The products of the present invention can be polymerized to make three distinct classes of products. The first conforming to the following structure:

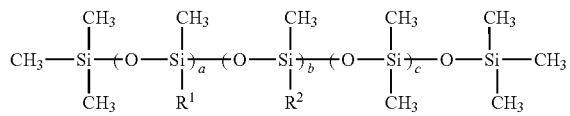

wherein
$R^1$ is —$(CH_2)_2$—$(CF_2)_8$—$CF_3$
$R^2$ is
    —$(CH_2)_3$—O—C(O)—CH=$CH_2$
a is an integer ranging from 1 to 20;
b is 1;
c is 0.

This monomer features a high level of fluoro in the compound, has one functional group and therefore has no crosslinking and has no silicone units, that tend to dilute the fluoro concentration. Compounds of this class are have a very low surface tension (below 20), have fluoro polymer attributes and repel silicone oil and water. The most interesting products in this group are homo-polymers, that is products having no other monomers present.

Class 2 Monomer
The second class conforming to the following structure:

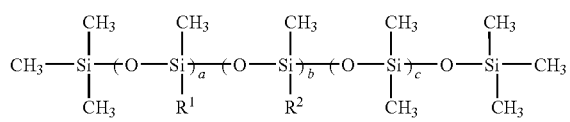

wherein
$R^1$ is —$(CH_2)_2$—$(CF_2)_8$—$CF_3$
$R^2$ is
    —$(CH_2)_3$—O—C(O)—CH=$CH_2$
a is an integer ranging from 5 to 20;
b is an integer ranging from 2 to 4;
c is an integer ranging from 5 to 20.

This monomer features a high level of fluoro in the compound, has more than one functional group and therefore has crosslinking and also has silicone units, these monomers and polymers made there from tend to be used in hetero-polymers as modifiers to add a low surface energy coating to surfaces. They are fluoropiliic (literally fluoro loving) materials.

Class 3 Monomer
The third class of products conform to the following structure:

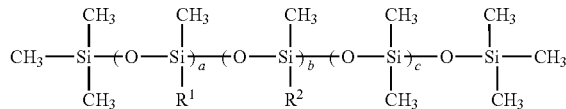

wherein
$R^1$ is —$(CH_2)_2$—$(CF_2)_8$—$CF_3$
$R^2$ is
    —$(CH_2)_3$—O—C(O)—CH=$CH_2$
a is an integer ranging from 1 to 5;
b is an integer ranging from 1;
c is an integer ranging from 10 to 20.

This monomer features a moderate level of fluoro in the compound, has one functional group and therefore has no crosslinking and has a high concentration of silicone units, that tend to dilute the fluoro concentration. Compounds of this class have silicone like functionality, surface tension around 25 and have outstanding slip. These materials are siliphilic that is they have silicone like properties.

Another aspect of the compounds of the present invention are polymers conforming to the following structure:

$$(-\!\!-\!\!(CH_2-CH)_x-\!\!+\!\cdots\!-\!CH_2-C(CH_3))_y\cdots)_z$$
$$\phantom{xxxxxxx}|\phantom{xxxxxxxxxxxxx}|$$
$$\phantom{xxxxxxx}A\phantom{xxxxxxxxxxxxx}B$$

A is $$CH_3-\underset{\underset{CH_3}{|}}{\overset{\overset{CH_3}{|}}{Si}}-(O-\underset{\underset{R^1}{|}}{\overset{\overset{CH_3}{|}}{Si}})_a-(O-\underset{\underset{(CH_2)_3}{|}}{\overset{\overset{CH_3}{|}}{Si}})_b-(O-\underset{\underset{CH_3}{|}}{\overset{\overset{CH_3}{|}}{Si}})_c-O-\underset{\underset{CH_3}{|}}{\overset{\overset{CH_3}{|}}{Si}}-CH_3$$
$$\phantom{xxxxxxxxxxxxxxxxxxxxxxxxxxxxx}|$$
$$\phantom{xxxxxxxxxxxxxxxxxxxxxxxxxxxxx}OC(O)-$$

wherein
$R^1$ is —$(CH_2)_2$—$(CF_2)_8$—$CF_3$
a is an integer ranging from 1 to 20;
b is an integer ranging from 1 to 4;
c is an integer ranging from 0 to 20;
B is
—$C(O)OR^3$
$R^3$ is all having 4 to 20 carbon atoms;
x is an integer ranging from 1 to 100;
y is an integer ranging from 0 to 100;
z is an integer ranging from 50 to 50,000.

Preferred Embodiment

One improved embodiment the monomer conforms to the following structure:

$$CH_3-\underset{\underset{CH_3}{|}}{\overset{\overset{CH_3}{|}}{Si}}-(O-\underset{\underset{R^1}{|}}{\overset{\overset{CH_3}{|}}{Si}})_a-(O-\underset{\underset{R^2}{|}}{\overset{\overset{CH_3}{|}}{Si}})_b-(O-\underset{\underset{CH_3}{|}}{\overset{\overset{CH_3}{|}}{Si}})_c-O-\underset{\underset{CH_3}{|}}{\overset{\overset{CH_3}{|}}{Si}}-CH_3$$

wherein
$R^1$ is —$(CH_2)_2$—$(CF_2)_8$—$CF_3$
$R^2$ is
—$(CH_2)_3$—O—C(O)—CH=$CH_2$
a is an integer ranging from 1 to 20;
b is 1;
c is an integer ranging from 0.

In another preferred embodiment the monomer conforms to the following structure:

$$CH_3-\underset{\underset{CH_3}{|}}{\overset{\overset{CH_3}{|}}{Si}}-(O-\underset{\underset{R^1}{|}}{\overset{\overset{CH_3}{|}}{Si}})_a-(O-\underset{\underset{R^2}{|}}{\overset{\overset{CH_3}{|}}{Si}})_b-(O-\underset{\underset{CH_3}{|}}{\overset{\overset{CH_3}{|}}{Si}})_c-O-\underset{\underset{CH_3}{|}}{\overset{\overset{CH_3}{|}}{Si}}-CH_3$$

wherein
$R^1$ is —$(CH_2)_2$—$(CF_2)_8$—$CF_3$
$R^2$ is
—$(CH_2)_3$—O—C(O)—CH=$CH_2$
a is an integer ranging from 5 to 20;
b is an integer ranging from 2 to 4;
c is an integer ranging from 5 to 20.

In still another preferred embodiment the monomer conforms to the following structure:

$$CH_3-\underset{\underset{CH_3}{|}}{\overset{\overset{CH_3}{|}}{Si}}-(O-\underset{\underset{R^1}{|}}{\overset{\overset{CH_3}{|}}{Si}})_a-(O-\underset{\underset{R^2}{|}}{\overset{\overset{CH_3}{|}}{Si}})_b-(O-\underset{\underset{CH_3}{|}}{\overset{\overset{CH_3}{|}}{Si}})_c-O-\underset{\underset{CH_3}{|}}{\overset{\overset{CH_3}{|}}{Si}}-CH_3$$

wherein
$R^1$ is —$(CH_2)_2$—$(CF_2)_8$—$CF_3$
$R^2$ is
—$(CH_2)_3$—O—C(O)—CH=$CH_2$
a is an integer ranging from 1 to 5;
b is 1
c is an integer ranging from 10 to 20.

In a preferred embodiment y is 0.

Examples

Raw Materials

Raw materials useful in the preparation of the compounds of the present invention are available from Siltech LLC and conform to the following structure:

$$CH_3-\underset{\underset{CH_3}{|}}{\overset{\overset{CH_3}{|}}{Si}}-(O-\underset{\underset{R^1}{|}}{\overset{\overset{CH_3}{|}}{Si}})_a-(O-\underset{\underset{R^3}{|}}{\overset{\overset{CH_3}{|}}{Si}})_b-(O-\underset{\underset{CH_3}{|}}{\overset{\overset{CH_3}{|}}{Si}})_c-O-\underset{\underset{CH_3}{|}}{\overset{\overset{CH_3}{|}}{Si}}-CH_3$$

wherein
$R^1$ is —$(CH_2)_2$—$(CF_2)_8$—$CF_3$
$R^3$ is —$(CH_2)_3$—OH
a is an integer ranging from 1 to 20;
b is an integer ranging from 1 to 4;
c is an integer ranging from 0 to 20.

Class 1

| Example | a | b | c |
|---------|-----|---|---|
| 1 | 1 | 1 | 0 |
| 2 | 5 | 1 | 0 |
| 3 | 10 | 1 | 0 |
| 4 | 15 | 1 | 0 |
| 5 | 20 | 1 | 0 |

Class 2

| Example | a | b | c |
|---------|-----|---|-----|
| 6 | 5 | 2 | 0 |
| 7 | 20 | 3 | 20 |
| 8 | 10 | 4 | 5 |
| 9 | 15 | 2 | 15 |

Class 3

| Example | a | b | c |
|---------|---|---|---|
| 10 | 1 | 1 | 10 |
| 11 | 3 | 1 | 20 |
| 12 | 5 | 1 | 15 |

Example 13

Acrylic Acid

Acrylic acid is an item of commerce and conforms to the following structure:

$CH_2=CH-C(O)OH$

CAS Number 79-10-7

Acrylate Esters

Acrylate Esters are made according to the following reaction sequence:

To the specified number of grams of the specified hydroxy compounds (Examples 1-12) is added 186 grams of Acrylic Acid (Example 13). Next is added 0.2% by weight of Dimethyltin Dichloride/Tetramethyldiacetoxydistannoxane, (2:1). The reaction mixture is then placed under vacuum and that vacuum relieved with nitrogen to remove traces of oxygen. The reaction mass is heated to 140 C and methanol distills off. There is a condenser placed in a vertical position above the reaction vessel. Cooling water is used to control the temperature of the top of the column to insure methanol is distilled off. The heating is controlled keeping the temperature at the column head at 100° C. maximum.

After about 8 hours the hydroxyl value is vanishingly low. The excess acrylic acid is removed by washing. The product is the oil phase.

| | Hydroxy Compound | |
|---|---|---|
| Example | Example | Grams |
| 14 | 1 | 573 |
| 15 | 2 | 1733 |
| 16 | 3 | 3183 |
| 17 | 4 | 1733 |
| 18 | 5 | 865 |
| 19 | 6 | 926 |
| 20 | 7 | 2600 |
| 21 | 8 | 978 |
| 22 | 9 | 1481 |
| 23 | 10 | 1313 |
| 24 | 11 | 2633 |
| 25 | 12 | 2843 |

Polymers of the Present Invention

Examples

Polymers of the Present Invention

The polymers of the present invention are prepared by reacting acrylate monomers shown above, alone or in combination with other monomers, in a cosmetically acceptable solvent is used. By cosmetically acceptable is meant the solvent has no mal odor. Finally a free radical initiator is added. Free radical imitators are well known in the art. Preferred initiators are selected from the group consisting of t-amyl peroctoate, benzoyl peroxide, azobisisobutrylnitrile and mixtures thereof.

Example 26

| Material | Weight % |
|---|---|
| Isododecane | 48.0 |
| Example 14 | 51.0 |
| T-amyl peroctoate | 1.0 |

Example 27

| Material | Weight % |
|---|---|
| Isododecane | 48.0 |
| Example 15 | 51.0 |
| T-amyl peroctoate | 1.0 |

The contents were added to a reaction vessel, heated to 250° F. and reacted to greater than 99.8% conversion.

Example 28

| Material | Weight % |
|---|---|
| Isododecane | 48.0 |
| Example 16 | 51.0 |
| T-amyl peroctoate | 1.0 |

The contents were added to a reaction vessel, heated to 250° F. and reacted to greater than 99.8% conversion.

Example 29

| Material | Weight % |
|---|---|
| Isododecane | 48.0 |
| Example 17 | 51.0 |
| T-amyl peroctoate | 1.0 |

The contents were added to a reaction vessel, heated to 250° F. and reacted to greater than 99.8% conversion.

Example 30

| Material | Weight % |
|---|---|
| Isododecane | 48.0 |
| Example 18 | 51.0 |
| T-amyl peroctoate | 1.0 |

The contents were added to a reaction vessel, heated to 250° F. and reacted to greater than 99.8% conversion.

Example 31

| Material | Weight % |
| --- | --- |
| Isododecane | 48.0 |
| Example 19 | 51.0 |
| T-amyl peroctoate | 1.0 |

The contents were added to a reaction vessel, heated to 250° F. and reacted to greater than 99.8% conversion.

Example 32

| Material | Weight % |
| --- | --- |
| Isododecane | 48.0 |
| Example 20 | 51.0 |
| T-amyl peroctoate | 1.0 |

The contents were added to a reaction vessel, heated to 250° F. and reacted to greater than 99.8% conversion. and reacted to greater than 99.8% conversion.

Example 33

| Material | Weight % |
| --- | --- |
| Isododecane | 48.0 |
| Example 21 | 51.0 |
| T-amyl peroctoate | 1.0 |

The contents were added to a reaction vessel, heated to 250° F. and reacted to greater than 99.8% conversion.

Example 34

| Material | Weight % |
| --- | --- |
| Isododecane | 48.0 |
| Example 22 | 51.0 |
| T-amyl peroctoate | 1.0 |

The contents were added to a reaction vessel, heated to 250° F. and reacted to greater than 99.8% conversion.

Example 35

| Material | Weight % |
| --- | --- |
| Isododecane | 48.0 |
| Example 23 | 51.0 |
| T-amyl peroctoate | 1.0 |

The contents were added to a reaction vessel, heated to 250° F. and reacted to greater than 99.8% conversion.

Example 36

| Material | Weight % |
| --- | --- |
| Isododecane | 48.0 |
| Example 24 | 51.0 |
| T-amyl peroctoate | 1.0 |

The contents were added to a reaction vessel, heated to 250° F. and reacted to greater than 99.8% conversion.

Example 37

| Material | Weight % |
| --- | --- |
| Isododecane | 48.0 |
| T-butyl methacrylate | 41.0 |
| Example 14 | 5.0 |
| Behenyl methacrylate | 5.0 |
| T-amyl peroctoate | 1.0 |

The contents were added to a reaction vessel, heated to 250° F. and reacted to greater than 99.8% conversion.

Example 38

| Material | Weight % |
| --- | --- |
| Isododecane | 48.0 |
| T-butyl methacrylate | 21.0 |
| Iso-butyl methacrylate | 10.0 |
| Example 15 | 10.0 |
| Behenyl methacrylate | 10.0 |
| t-amyl peroctoate | 1.0 |

The contents were added to a reaction vessel, heated to 250° F. and reacted to greater than 99.8% conversion.

Example 39

| Material | Weight % |
| --- | --- |
| Isododecane | 48.0 |
| iso-butyl methacrylate | 36.0 |
| Example 16 | 5.0 |
| Behenyl methacrylate | 10.0 |
| t-amyl peroctoate | 1.0 |

The contents were added to a reaction vessel, heated to 250° F. and reacted to greater than 99.8% conversion.

Example 40

| Material | Weight % |
| --- | --- |
| Isododecane | 48.0 |
| Example 17 | 5.0 |
| T-butyl methacrylate | 41.0 |
| Stearyl methacrylate | 5.0 |
| t-amyl peroctoate | 1.0 |

The contents were added to a reaction vessel, heated to 250° F. and reacted to greater than 99.8% conversion.

Example 41

| Material | Weight % |
| --- | --- |
| Isododecane | 48.0 |
| Example 18 | 1.0 |
| T-butyl methacrylate | 40.0 |
| Behenyl methacrylate | 10.0 |
| Vazo 67 | 1.0 |

The contents were added to a reaction vessel, heated to 250° F. and reacted to greater than 99.8% conversion.

Example 42

| Material | Weight % |
| --- | --- |
| Isododecane | 48.0 |
| T-butyl methacrylate | 39.0 |
| Example 19 | 2.0 |
| Behenyl methacrylate | 10.0 |
| Benzoyl Peroxide | 1.0 |

The contents were added to a reaction vessel, heated to 210° F. and reacted to greater than 99.8% conversion.

Example 43

| Material | Weight % |
| --- | --- |
| IN-2 Isononyl Isononoate | 48.0 |
| Example 20 | 10.0 |
| T-butyl methacrylate | 31.0 |
| Behenyl methacrylate | 10.0 |
| Benzoyl Peroxide | 1.0 |

The contents were added to a reaction vessel, heated to 210° F. and reacted to greater than 99.8% conversion.

Example 44

| Material | Weight % |
| --- | --- |
| Isododecane | 28.0 |
| T-butyl methacrylate | 61.0 |
| Behenyl methacrylate | 5.0 |
| Example 21 | 5.0 |
| t-amyl peroctoate | 1.0 |

The contents were added to a reaction vessel, heated to 250° F. and reacted to greater than 99.8% conversion.

Example 45

| Material | Weight % |
| --- | --- |
| Isododecane | 48.0 |
| T-butyl methacrylate | 1.0 |
| Example 22 | 1.0 |
| Iso-butyl methacrylate | 29.0 |
| Behenyl methacrylate | 20.0 |
| t-amyl peroctoate | 1.0 |

The contents were added to a reaction vessel, heated to 250° F. and reacted to greater than 99.8% conversion.

Example 46

| Material | Weight % |
| --- | --- |
| Isododecane | 48.0 |
| Example 23 | 5.0 |
| Iso-butyl methacrylate | 11.0 |
| Behenyl methacrylate | 35.0 |
| t-amyl peroctoate | 1.0 |

The contents were added to a reaction vessel, heated to 250° F. and reacted to greater than 99.8% conversion.

Example 47

| Material | Weight % |
| --- | --- |
| Isododecane | 48.0 |
| T-butyl methacrylate | 11.0 |
| Example 24 | 10.0 |
| Stearyl methacrylate | 30.0 |
| t-amyl peroctoate | 1.0 |

The contents were added to a reaction vessel, heated to 250° F. and reacted to greater than 99.8% conversion.

Example 48

| Material | Weight % |
| --- | --- |
| Isododecane | 48.0 |
| Example 14 | 1.0 |
| T-butyl methacrylate | 10.0 |

| Material | Weight % |
| --- | --- |
| Behenyl methacrylate | 40.0 |
| Benzoyl Peroxide | 1.0 |

The contents were added to a reaction vessel, heated to 210° F. and reacted to greater than 99.8% conversion.

Example 49

| Material | Weight % |
| --- | --- |
| Isononyl Isononoate | 48.0 |
| Example 15 | 5.0 |
| T-butyl methacrylate | 16.0 |
| Behenyl methacrylate | 30.0 |
| Benzoyl Peroxide | 1.0 |

The contents were added to a reaction vessel, heated to 210° F. and reacted to greater than 99.8% conversion.

Example 50

| Material | Weight % |
| --- | --- |
| Isononyl Isononoate | 48.0 |
| Example 16 | 5.0 |
| T-butyl methacrylate | 16.0 |
| Behenyl methacrylate | 30.0 |
| Benzoyl Peroxide | 1.0 |

The residual monomers were determined by Gas Chromatography/Mass Spectroscopy. All polymers had residual monomer levels below 2000 ppm.

Applications Information

The compounds of the present invention are silicone fluoro acrylates. They possess low surface tension (below 25 dynes/cm2), they spread on surfaces to form oil resistant films. These properties make the compounds of the present invention useful in pigmented products like lipstick where they provide outstanding spread, uniformity of color and transfer resistance.

An example of such a lipstick is:

Transfer Resistant Lipstick

| INCI Name | % |
| --- | --- |
| Triisostearyl Citrate | 5.00 |
| Polyglyceryl-3 Diisostearate | 0.50 |
| Carnauba | 6.50 |
| Ozokerite (m.p. 80° C.) | 16.00 |
| Microcrystalline Wax | 6.00 |
| Polyethylene | 1.00 |
| Isododecane | 35.00 |
| Example 8 | 10.00 |
| Bismuth Oxychloride | 6.00 |
| Mica, Methicone | 9.00 |

| | % |
| --- | --- |
| Color Grind | |
| Red 6 Lake | 0.40 |
| Red 7 Lake | 0.20 |
| Titanium Dioxide | 0.33 |
| Iron Oxides (yellow) | 0.10 |
| Iron Oxides (red) | 0.17 |
| Triisostearyl Citrate | 3.80 |
| | 100.00 |

Manufacturing Procedure:

Prepare color grind in advance, by combining the oil and pigment with stirring. Mill over a three roll mill until the agglomerates are reduced to under 10 μm.

Combine the waxes and oils in a closed kettle equipped with a high speed agitator and a side sweep mixer. Heat to 95-100° C. with stirring until clear. Add the Biron LF-2000 and the D;9051/I. Mill at high speed until dispersed. Add the color grind. Mill at high speed for one minute. Stir batch, allowing it to cool to 70° C. Drop the batch or proceed directly to fill into suitable hermetically sealed cases.

Additionally make up products benefit from the use of the compositions of the present invention. The incorporation of the compounds into make up products results in better dispersion of the pigment anf more stabe emulsions.

Typical make up formulations are:

| Part | | % |
| --- | --- | --- |
| A | Water | 38.60 |
| A | Cetyl hydroxyethylcellulose Polysurf 67 CS | 0.20 |
| A | Propylene Glycol | 2.00 |
| A | Na2 EDTA | 0.10 |
| A | NaCl | 1.00 |
| B | Color Blend | 15.00 |
| C | Lauryl Peg 8 dimethicone (Siltech J208-812) | 5.00 |
| C | Octyldodecyl Neopentanoate | 17.50 |
| C | Example 8 | 5.00 |
| C | Propylparaben | 0.20 |
| C | Methylparaben | 0.40 |
| D | Cyclomethicone Pentamer | 15.00 |
| | | 100.00 |
| | Viscosity LVF #3 at 30 RPM | 5,700 |

Heat ⅓ of water to 75° C. or higher. Add Polysurf with vigorous mixing and continue mixing until completely dispersed.

Add remaining water to mixture and allow to cool to 35° C. while continuing to mix.

Add remaining Part A ingredients and mix until uniform.

Add part B and disperse in part A until uniform.

Heat part A to 60° C.

Heat part C to 70° C. and mix until all solids are dissolved

Add part D to part C, maintain temperature of combined phase at 65° C.

Add Part AB to part CD with high speed propeller mixer.

Cool to 30° C. and fill.

| Color Blends | |
|---|---|
| Titanium Dioxide | 10.02 |
| Yellow Iron Oxide | 0.96 |
| Red Iron Oxide | 0.29 |
| Black Iron Oxide | 0.08 |
| Kaolin USP | 2.25 |
| Excel Talc | 1.40 |
| | 15.00 |

Mix and blend to form dry extender.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A fluoro silicone acrylate conforming to the following structure:

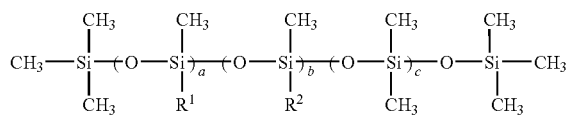

wherein
R$^1$ is —(CH$_2$)$_2$—(CF$_2$)$_8$—CF$_3$
R$^2$ is
    —(CH$_2$)$_3$—O—C(O)—CH=CH$_2$
a is an integer ranging from 1 to 20;
b is an integer ranging from 1 to 4;
c is an integer ranging from 0 to 20.

2. A fluoro acrylate of claim 1 wherein
a is an integer ranging from 1 to 20;
b is 1;
c is 0.

3. A fluoro acrylate of claim 1 wherein:
a is an integer ranging from 5 to 20;
b is an integer ranging from 2 to 4;
c is an integer ranging from 5 to 20.

4. A fluoro acrylate of claim 1 wherein:
a is an integer ranging from 1 to 5;
b is an integer ranging from 1;
c is an integer ranging from 10 to 20.

* * * * *